United States Patent [19]

Eckland

[11] Patent Number: 5,055,041
[45] Date of Patent: Oct. 8, 1991

[54] ALVEOLAR PRESSURE INDICATOR DEVICE

[76] Inventor: Gerald Eckland, P.O. Box 3339, Smithers, British Columbia, V0J 2N0, Canada

[21] Appl. No.: 464,325

[22] Filed: Jan. 12, 1990

[30] Foreign Application Priority Data

Nov. 25, 1989 [CA] Canada .............................. 2,003,855

[51] Int. Cl.⁵ ..................... A62C 11/00; A62C 19/04
[52] U.S. Cl. ....................................... 433/56; 433/54; 433/72
[58] Field of Search ...................... 433/53, 54, 55, 56, 433/57, 72, 73, 25, 52, 49, 65, 215, 229; 33/513, 514; 73/865.6

[56] References Cited

U.S. PATENT DOCUMENTS 2,235,524  8/1937  Lentz ................................... 433/56
2,937,443  5/1960  Skinner ............................... 433/72

FOREIGN PATENT DOCUMENTS 303069  8/1971  U.S.S.R. .............................. 433/72

Primary Examiner—John J. Wilson
Assistant Examiner—Cindy A. Cherichetti
Attorney, Agent, or Firm—Sixbey, Friedman, Leedom and Ferguson

[57] ABSTRACT

A device for measuring pressure transmitted to the mandibular alveolar ridge as well as the amount of applied pressure necessary to shear off various types of food, in full upper and lower dentures. The device comprises a denture-receiving articulator to which a measured pressure is applied to upper dentures and the pressure then transmitted to the lower dentures to be measured.

10 Claims, 2 Drawing Sheets

ALVEOLAR PRESSURE INDICATOR DEVICE

FIELD OF THE INVENTION

The present invention relates to a device for measuring pressure transmitted to the mandibular alveolar ridge as well as the amount of applied pressure necessary to shear off various types of food, in full upper and lower dentures.

BACKGROUND OF THE INVENTION

Until now there has been very little in the way of apparatus developed for dentists or denturists to ascertain the efficacy of dentures. In particular, it would be of interest to dentists or denturists supplying dentures for a patient, to ascertain the ridge pressures for different types of dentures to thereby establish which design of posterior teeth will create the least pressure on the lower mandibular, denture-bearing ridge. As well, it would be of interest to a dentist or denturist to know, for different constructions of dentures, the pressure developed on that ridge as different types of food are sheared.

It is an object of the present invention to provide such an apparatus.

SUMMARY OF THE INVENTION

In accordance with the present invention a device for measuring pressure transmitted to the mandibular alveolar ridge and for indicating the amount of applied pressure necessary to shear off various types of food, in full upper and lower dentures is provided. The device comprises an articulator having upper and lower frames to pivot between open and closed positions simulating opening and closing jaw movements. Means are associated with the upper and lower frames to releasably secure thereto conventional upper and lower support bases which correspond respectively to denture-receiving upper and lower dental arches. Means are also provided to releasably secure upper and lower dentures respectively to the upper and lower support bases. Means are associated with the lower support base to transmit pressure applied on the support base from lower dentures when in position thereon to a position below the lower support base. Means are provided to apply a predetermined pressure to the upper frame when in closed position with upper and lower dentures secured in the device. Pressure gauge means are mechanically associated with the lower support base to measure pressure exerted on this lower support base as transmitted through the upper and lower dentures during the acts of shearing and occluding by the pressure transmitting means.

In a preferred embodiment of the present invention, the pressure gauge means comprises a pair of sphygmomanometer tubes, one on each side embedded in the lower support base, and a sphygmomanometer gauge means which is associated with each of the sphygmomanometer tubes. A squeeze bulb is associated with each of the sphygmomanometer tubes to enable pressure to be accumulated in the sphygmomanometer tube. The pressure transmitting means comprises portions of the lower support base on each side which portions are detached from the remaining portion of the support base so as to be supported at their normal height by the sphygmomanometer tubes on each side to become increasingly downwardly displaced as pressure on a lower denture in the device increases.

The device according to the present invention provides a reasonably accurate measurement of ridge pressures for different types of dentures which may be tested by the device. As well, the pressure on the ridge required to be applied to shear a bolus of food between the teeth of the dentures may be readily determined using the device.

BRIEF DESCRIPTION OF THE DRAWINGS

These and other objects and advantages of the invention will become apparent upon reading the following detailed description and upon referring to the drawings in which.

Figure 1:
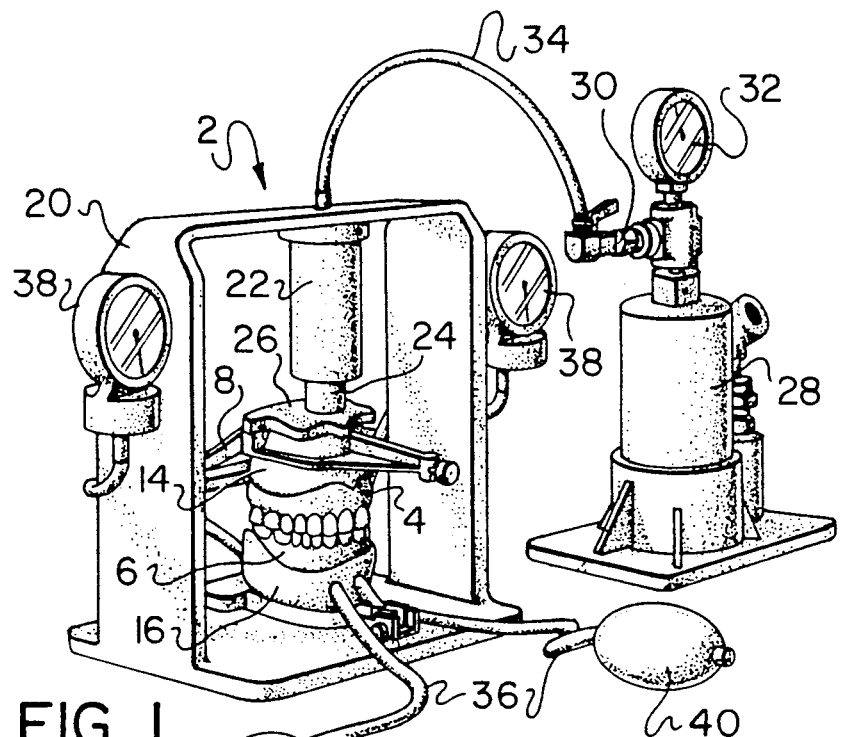
FIG. 1 is a perspective view of a device for measuring pressure transmitted to the mandibular alveolar ridge in accordance with the present invention.

While the invention will be described in conjunction with example embodiments, it will be understood that it is not intended to limit the invention to such embodiments. On the contrary, it is intended to cover all alternatives, modifications and equivalents as may be included within the spirit and scope of the invention as defined by the appended claims.

DETAILED DESCRIPTION OF THE DRAWINGS

In the drawings, similar features have been given similar reference numerals.

Turning to FIG. 1, there is illustrated a device 2 for measuring pressure transmitted to the mandibular alveolar ridge by upper dentures 4 and lower dentures 6. A conventional articulator 8 for holding dentures is provided, with upper frames 10 and lower frames 12 pivoting between open position (FIG. 2) and closed position (FIGS. 1 and 3), to simulate jaw movements. Conventional upper and lower support bases 14 and 16 are secured respectively to upper and lower frames 10 and 12, for receiving (respectively) upper and lower dentures 4 and 6. These upper and lower support bases 14 and 16 correspond respectively to upper and lower dental arches in a person's mouth. Upper and lower dentures 4 and 6 are releasably secured in place on upper and lower support bases 14 and 16 by friction or by appropriate securing or clamp means 18.

Articulator 8 is held in operative position within a circumscribing frame 20. To the top of frame 20 is mounted a pressure applicator means in the form of an hydraulic cylinder 22 with a ram 24 extending from the lower end thereof, to move vertically upward and downward. A pressure plate 26 is secured to the top of upper frame 10, to receive the lower end of ram 24 as illustrated. Hydraulic pump 28 with appropriate valve control means 30 and pressure gauge 32 is provided to enable the supply of a predetermined pressure to cylinder 22 through line 34. In this manner, when upper and lower dentures 4 and 6 are in position on upper and lower support bases 14 and 16, with articulator 8 in closed position, a predetermined amount of pressure can be applied to the upper dentures 4 onto lower dentures 6.

Figure 2:
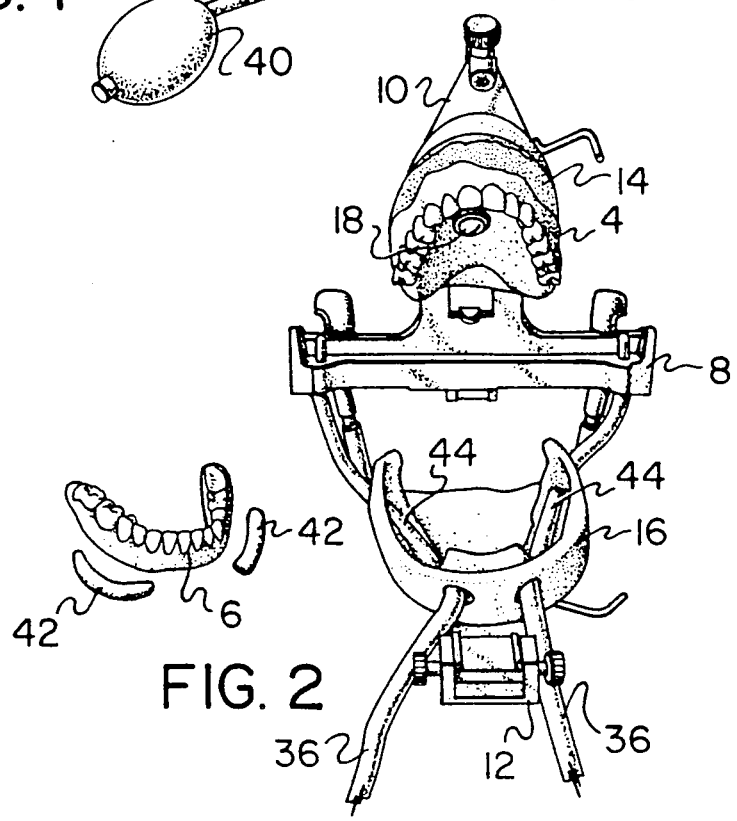
FIG. 2 is an exploded, partial front view of the device of FIG. 1 in open position.
Figure 3:
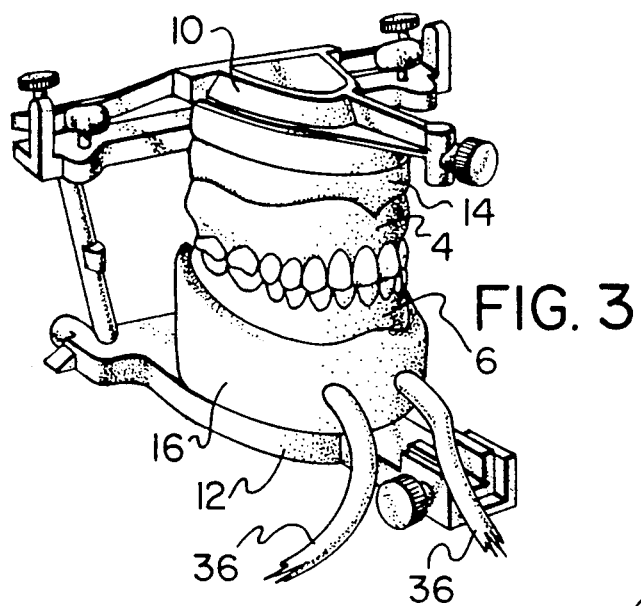
FIG. 3 is a front, partial view of the device of FIG. 1, in closed, pressure measuring position.

As can be seen in FIG. 2, within lower support base 16, on either side is set a pressure measuring tube 36, which, in the illustrated embodiment, may be a conventional sphygmomanometer tube. A sphygmomanometer gauge 38 is associated with each sphygmomanometer tube 36, and mounted on frame 20 as illustrated. A squeeze bulb 40 is also provided for each sphygmomanometer tube 36 to pressurize that tube as required. The posterior portion of each side of lower support base 16 has an elongated, upper portion 42 thereof cutaway from the remaining portion, these portions 42 formed so as to be supported by corresponding portions 44 of sphygmomanometer tubes 36 at their normal height in the support base. In this manner, when lower dentures 6 are in position (FIGS. 1 and 3), with ram 24 applying pressure on upper dentures 4 through upper frame 10, that pressure which is transmitted to lower denture 6 is then further transmitted, through portions 42 of lower support base 16 to sphygmomanometer tubes 36 so that the pressure being transmitted to the mandibular alveolar ridge, on either side, can be ascertained through gauges 38.

Different sets of dentures 4 and 6, all fitting the same upper and lower support bases 14 and 16 precisely, and each having different design styles of teeth such as plastic and porcelain 33° and 0° teeth, may be tested in this manner.

Figure 4:
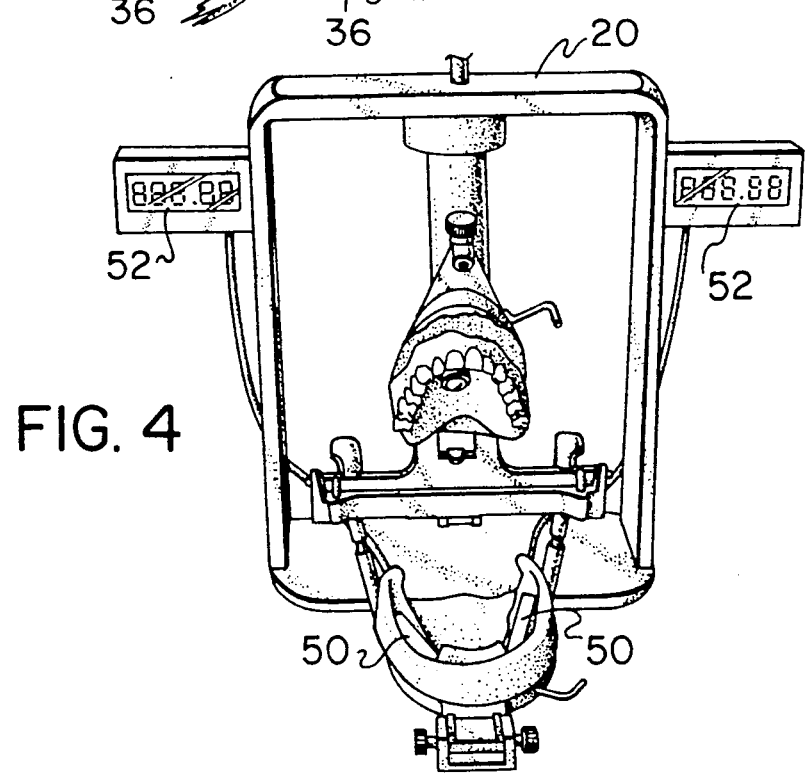
FIG. 4 is a schematic perspective view of an alternative embodiment of the present invention.

In the alternative embodiment illustrated in FIG. 4, instead of a sphygmomanometer tube 36, a strain gauge 50 may be appropriately seated beneath each portion 42, with an appropriate read-out means 52 being provided. Other pressure sensing devices such as electronic sensors may be used. As well, instead of gauges as illustrated, electronic digital read-out devices may be used to convert the pressure transmitted to lower support base 16 to an appropriate pressure read-out. Such modifications will be obvious to those skilled in the art. Moreover, in such modifications, it may not be necessary to have cut-out portions 42 in the lower support base 16. It is envisaged that lower support base 16, for example, may be made integrally from an appropriate pressure transmitting material so that the pressure transmitted may be communicated directly to a pressure reading means, without having to rely on the displacement of portions 42.

In the device in accordance with the present invention, it will be understood that that device also indicates, by way of gauge 32, the amount of applied pressure necessary for different types of denture teeth to shear off various types of food, and the relative resulting pressure (through gauges 38) consequently applied to the mandibular alveolar ridge in each instance.

An example of the operation of this device will now be provided.

EXAMPLE

The sphygmomanometer tubes 36 are pressured up to a common arbitrary pressure on both sides of the lower dental arch, by the squeeze bulbs 40 and held at that pressure. The starting pressure on the tubes 36, below portions 42 is then recorded. This pressure will be indicated in mm's of mercury on the sphygmomanometer gauges 38.

The articulator 8 is then closed so that the denture teeth come into occlusal contact up to a fixed pressure. This pressure is achieved by the hydraulic cylinder 22, which is mounted above the articulator 8 in the frame 20, and is activated by the hydraulic pump 28. This pressure indicated on pressure gauge 32 on the pump 28 and recorded.

Each set of dentures 4 and 6, which fit the acrylic models of the mandibular alveolar ridge by friction in the same way, are closed into occlusion to the same applied pressure. When the desired hydraulic pressure is achieved, the resulting pressure on the sphygmomanometer tubes 36 is registered on the sphygmomanometer gauges 38 and recorded.

The difference between the pressures is then recorded.

This procedure is done with each set of dentures 4 and 6 available, for example 0° plastic posteriors, 0° porcelain posteriors, 33° plastic posteriors and 33° porcelain posteriors.

A similar procedure is then repeated with Melba Toast (Trade Mark) as a bolus of food between the posterior teeth of each set of dentures. In this application, the necessary shearing pressure, i.e. the pressure required to be applied by the hydraulic cylinder 22 to shear the Melba Toast (Trade Mark) completely off is recorded, as well as the difference in pressure on the sphygmomanometer tubes 36, which is registered on the sphygmomanometer gauges 38, between starting pressure in column mm's of mercury and whatever it may be when shearing pressure is achieved.

In this manner it can be established which design of posterior teeth and which material of posterior teeth create the most or the least pressure on the lower (mandibular, alveolar, denture bearing) ridge in each instance, with and without a bolus of food between the teeth.

Table 1 sets out some test results, in accordance with this procedure, for different types of dentures, a bolus of food being held between the teeth in those instances where a shearing DS reading has been indicated.

TABLE 1

| TEETH | APPLIED P.S.I. (lbs) | mmHg START Left/Right | mmHg END Left/Right | mmHg DIFFERENCE Left/Right | SHEARING P.S.I. (lbs) |
|---|---|---|---|---|---|
| Plastic 33° | 160 | 275 | 281 | 6 | |
| Plastic 33° | 160 | 275 | 281 | 6 | |
| Porcelain 33° | 140 | 280 | 285 | 5 | |
| Porcelain 33° | 160 | 280 | 285 | 5 | |
| Plastic 33° | 168 | 271 | 278 | 7 | |
| Plastic 33° | 160 | 271 | 278 | 7 | |
| Porcelain 33° | 140 | 270 | 276 | 6 | |

TABLE 1-continued

| TEETH | APPLIED P.S.I. (lbs) | mmHg START Left/Right | mmHg END Left/Right | mmHg DIFFERENCE Left/Right | SHEARING P.S.I. (lbs) |
|---|---|---|---|---|---|
| Porcelain 33° | 160 | 270 | 276 | 6 | |
| Plastic 33° | 160 | 258 | 268 | 10 | 200 |
| Plastic 33° | 160 | 260 | 269 | 9 | |
| Porcelain 33° | 160 | 261 | 268 | 7 | 130 |
| Porcelain 33° | 160 | 260 | 270 | 10 | |
| Plastic 33° | 170 | 217/219 | 224/223 | 7/4 | 130 |
| Plastic 33° | 170 | 219/220 | 225/229 | 6/9 | |
| Porcelain 33° | 170 | 213/216 | 220/221 | 7/5 | 95 |
| Porcelain 33° | 170 | 213/216 | 223/223 | 10/7 | |
| Plastic Bio-mech. (trade mark) | 110 | 213/217 | 220/227 | 7/10 | 110 |
| Plastic Bio-mech. (trade mark) | 170 | 213/216 | 221/225 | 8/9 | |
| Porcelain Bio-mech. (trade mark) | 170 | 214/216 | 222/221 | 8/5 | 90 |
| Porcelain Bio-mech. (trade mark) | 170 | 214/215 | 225/222 | 11/7 | |

It has been ascertained that the device 2 in accordance with the present invention will also indicate to a degree the self-cleaning ability of various design types of posterior teeth during lateral movements of mastication.

Thus it is apparent that there has been provided in accordance with the invention a device for measuring pressure transmitted to the mandibular alveolar ridge, as well as the amount of applied pressure necessary to shear off various types of food, in full upper and lower dentures that fully satisfies the objects, aims and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the invention.

What I claim as my invention:

1. A device for measuring pressure transmitted to the mandibular alveolar ridge and for indicating the amount of applied pressure necessary to shear off various types of food, in full upper and lower dentures, the device comprising:

(a) an articulator having upper and lower frames pivoting between open and closed positions to simulate opening and closing jaw movements;

(b) means associated with said upper and lower frames to releasably secure thereto conventional upper and lower support bases corresponding respectively to denture-receiving upper and lower dental arches;

(c) means to releasably secure upper and lower dentures respectively to the upper and lower support bases;

(d) pressure responsive means associated with the lower support base to response to pressure applied on the support base from lower dentures positioned thereon, the pressure responsive means comprising a sphygmomanometer tube positioned under the lower support base;

(e) means to apply a predetermined pressure to the upper frame when in closed position with upper and lower dentures secured in the device; and (f) pressure gauge means mechanically associated with said pressure responsive means of the lower support base to measure pressure exerted thereon as transmitted through the upper and lower dentures during the acts of shearing and occluding, the pressure gauge means comprising a sphygmomanometer gauge means associated with the sphygmomanometer tube for measuring the pressure within the tube.

2. A device according to claim 1 wherein the pressure gauge means comprises a pair of sphygmomanometer tubes, one on each side embedded in the lower support base, a sphygmomanometer gauge means associated with each of the sphygmomanometer tubes.

3. A device according to claim 2 wherein a squeeze bulb is associated with each of the sphygmomanometer tubes to enable pressure to be accumulated in the sphygmomanometer tube.

4. A device according to claim 3 wherein the pressure responsive means comprises portions of the lower support base on each side detached from the remaining portion of the support base so as to be supported at their normal height by the sphygmomanometer tubes on each side and become increasingly downwardly displaced as pressure on a lower denture in the device increases.

5. A device according to claim 1 wherein the means to apply pressure comprises a cylinder-actuated ram, the ram to act on the upper frame to apply pressure thereto when upper and lower dentures are in position in the device.

6. A device according to claim 5 wherein a pressure gauge is associated with the cylinder of the ram to indicate the pressure being exerted by the ram.

7. A device according to claim 5 wherein the ram acts on a pressure plate positioned between the cylinder and the upper frame, the pressure plate to bear against the upper frame under action of the ram.

8. A device according to claim 1 wherein the articulator and means to apply pressure on the upper frame are mounted on a support frame.

9. An extra-oral apparatus for measuring pressure likely to be transmitted to the mandibular alveolar ridge during use in a patient's mouth by a set of upper and lower dentures before the dentures are actually inserted into the patient's mouth, said apparatus comprising:
   (a) articulator means including upper and lower frames pivotally connected to pivot between open and closed positions for simulating jaw movements;
   (b) base securing means associated with each of said upper and lower frames for releasably securing to said frames an upper support base and a lower support base corresponding, respectively, to the upper and lower dental arches of a patient to be fitted with dentures;
   (c) denture securing means for releasably securing said upper and lower dentures to said upper and lower support bases;
   (d) pressure applying means for applying a predetermined pressure to the upper frame to cause said upper dentures to occlusally contact said lower dentures when said upper frame is in said closed position and said upper and lower dentures are secured in said support bases;
   (e) pressure sensing means associated with said lower support base for measuring the pressure exerted on said lower support base when said predetermined pressure is applied to said upper frame, wherein said pressure sensing means comprises a sphygmomanometer tube; and
   (f) pressure indicator means for indicating the pressure exerted on said lower support base so that the pressure likely to be transmitted to the patient's mandibular alveolar ridge when the dentures are in use can be determined, wherein said pressure indicator means comprises sphygmomanometer gauge means associated with the sphygmomanometer tube for indicating said pressure.

10. A device for measuring pressure transmitted to the mandibular alveolar ridge and for indicating the amount of applied pressure necessary to shear off various types of food, in full upper and lower dentures, the device comprising:
   (a) an articulator having upper and lower frames pivoting between open and closed positions to simulate opening and closing jaw movements;
   (b) means associated with said upper and lower frames to releasably secure thereto conventional upper and lower support bases corresponding respectively to denture-receiving upper and lower dental arches;
   (c) means to releasably secure upper and lower dentures respectively to the upper and lower support bases;
   (d) pressure responsive means associated with the lower support base to response to pressure applied on the support base from lower dentures positioned thereon, the pressure responsive means comprising a sphygmomanometer tube positioned under the lower support base;
   (e) means to apply a predetermined pressure to the upper frame when in closed position with upper and lower dentures secured in the device; and
   (f) pressure gauge means mechanically associated with said pressure responsive means of the lower support base to measure pressure exerted thereon as transmitted through the upper and lower dentures during the acts of shearing and occluding, said pressure gauge means comprising strain gauge means positioned beneath the pressure responsive means so as to indicate the pressure being exerted thereon.

* * * * *